United States Patent
Dadd et al.

(10) Patent No.: US 7,272,449 B2
(45) Date of Patent: *Sep. 18, 2007

(54) COCHLEAR IMPLANT ELECTRODE ARRAY

(75) Inventors: Fysh Dadd, Lane Cove (AU); Ian Darley, Lane Cove (AU); Peter Gibson, Lane Cove (AU); John Parker, Lane Cove (AU); Claudiu Treaba, Lane Cove (AU)

(73) Assignee: Cochlear Limited, Lane Cove, NSW (AU)

( * ) Notice: Subject to any disclaimer, the term of this patent is extended or adjusted under 35 U.S.C. 154(b) by 257 days.

This patent is subject to a terminal disclaimer.

(21) Appl. No.: 10/149,642
(22) PCT Filed: Sep. 28, 2001
(86) PCT No.: PCT/AU01/01231

§ 371 (c)(1),
(2), (4) Date: Nov. 13, 2003

(87) PCT Pub. No.: WO02/28473

PCT Pub. Date: Apr. 11, 2002

(65) Prior Publication Data

US 2004/0122501 A1    Jun. 24, 2004

(30) Foreign Application Priority Data

Oct. 4, 2000 (AU) .................................. PR0542
Oct. 17, 2000 (AU) .................................. PR0807
Oct. 25, 2000 (AU) .................................. PR1005
Nov. 29, 2000 (AU) .................................. PR1778

(51) Int. Cl.
*A61N 1/05*    (2006.01)
(52) U.S. Cl. ........................................ 607/137; 607/57
(58) Field of Classification Search ................ 607/137, 607/55–57, 136; 623/10; 600/25

See application file for complete search history.

(56) References Cited

U.S. PATENT DOCUMENTS 3,890,977 A    6/1975    Wilson
(Continued)

FOREIGN PATENT DOCUMENTS

EP    0002 068    11/1978
(Continued)

OTHER PUBLICATIONS

International Search Report; PCT/AU01/01231 (WO 02/28473) filed Sep. 28, 2001; Inventors: Dadd, Fysh et al. Applicant: Cochlear Limited.
(Continued)

*Primary Examiner*—Carl Layno
*Assistant Examiner*—Jessica L. Reidel
(74) *Attorney, Agent, or Firm*—Connolly Bove Lodge & Hutz, LLP (57) ABSTRACT

A cochlear implant electrode assembly (10) comprising an elongate electrode carrier member (11), a bioresorbable stiffening element (15) and an outer layer (16) surrounding the stiffening element (15). The carrier member (11) is made of a resiliently flexible first material and has a plurality of electrodes (12) mounted thereon and has a first configuration selected to allow it to be inserted into an implantee's cochlea, and at least a second configuration wherein it is curved to match a surface of the cochlea. The bioresorbable stiffening element (15) has a configuration selected for biasing the elongate member (11) into the first configuratin and is made of a second material relatively stiffer than the first material and which dissolves or softens on exposure to cochlear fluids to permit the elongate member (11) to at least approach or adopt the second configuration. The outer layer (16) surrounding the stiffening element (15) is made of a material sufficiently resiliently flexible to allow the elongate member (11) to at least approach or adopt the second configuration. The outer layer (16) has a first rate of cochlear fluid ingress therethrough and has at least one fluid ingress means (21) formed therein. The rate of cochlear fluid ingress through the fluid ingress means (21) is greater than the first rate of cochlear fluid ingress through the outer layer (16).

107 Claims, 3 Drawing Sheets

U.S. PATENT DOCUMENTS

| | | | |
|---|---|---|---|
| 4,046,151 A | | 9/1977 | Rose |
| 4,154,247 A | | 5/1979 | O'neil |
| 4,357,497 A | | 11/1982 | Hochmair et al. |
| 4,381,013 A | | 4/1983 | Dutcher |
| 4,532,930 A | | 8/1985 | Crosby et al. |
| 4,762,135 A | | 8/1988 | van der Puije et al. |
| 5,645,585 A | * | 7/1997 | Kuzma ................ 623/10 |
| 5,653,742 A | | 8/1997 | Parker et al. |
| 5,755,765 A | | 5/1998 | Hyde et al. |
| 5,769,077 A | * | 6/1998 | Lindegren ............. 600/373 |
| 5,782,744 A | * | 7/1998 | Money .................. 600/25 |
| 5,902,329 A | | 5/1999 | Hoffmann et al. |
| 6,038,484 A | | 3/2000 | Kuzma |
| 6,119,044 A | | 9/2000 | Kuzma |
| 6,304,787 B1 | * | 10/2001 | Kuzma et al. .......... 607/137 |
| 6,309,410 B1 | * | 10/2001 | Kuzma et al. .......... 607/137 |
| 6,421,569 B1 | | 7/2002 | Treaba et al. |
| 2003/0045921 A1 | | 3/2003 | Dadd et al. |
| 2004/0030376 A1 | | 2/2004 | Gibson et al. |
| 2004/0078057 A1 | | 4/2004 | Gibson |
| 2004/0116995 A1 | * | 6/2004 | Dadd ..................... 607/137 |
| 2004/0122501 A1 | | 6/2004 | Dadd et al. |

FOREIGN PATENT DOCUMENTS

| | | |
|---|---|---|
| EP | 0350 188 A1 | 6/1989 |
| EP | 0 602 859 A2 | 6/1994 |
| EP | 0 653 223 A2 | 5/1995 |
| EP | 0 739 642 A2 | 10/1996 |
| EP | 0 778 043 A1 | 12/1996 |
| EP | 0 778 044 A2 | 12/1996 |
| EP | 0 778 044 A3 | 12/1996 |
| EP | 0 773 037 A2 | 5/1997 |
| EP | 0 783 900 A2 | 7/1997 |
| EP | 0 784 994 A1 | 7/1997 |
| EP | 0784 995 A1 | 7/1997 |
| EP | 0 919 254 A2 | 6/1999 |
| EP | 0 783 901 B1 | 4/2003 |
| GB | 2 217 993 A | 11/1989 |
| WO | WO97/10784 A1 | 3/1997 |

OTHER PUBLICATIONS

Australian International-Type Search Report dated Dec. 20, 2000; related PR 0542 filed Oct. 1, 2000; Applicant: Cochlear Limited.
Australian International-Type Search Report dated Dec. 20, 2000; related PR 0807 filed Oct. 1, 2000; Applicant: Cochlear Limited.
Australian International-Type Search Report dated Dec. 20, 2000; related PR 1005 filed Oct. 1, 2000; Applicant: Cochlear Limited.
Research Disclosure, Nov. 1997, No. 403, p. 790-Article 40349, p. 791-Figures 1-2; "Epicardial-Transvenous Left Ventricular Lead With Dual Ring Electrodes (Cathode Ring And Anode Ring) Design"; Applicant/Inventor: Anonymous (Kenneth Mason Publications Ltd, Ernsworth, Hampshire, England); Comments on Relevance: Australia Search Report PR 1005.
Research Disclosure, Nov. 1997, No. 403, p. 785-Article 40342 with Figure 1; Epicardial-Transvenous Left Atrial Lead With Wound "Butterfly Tongue" Electrode; Applicant/Inventor: Anonymous (Kenneth Mason Publications Ltd, Ernsworth, Hampshire, England); Comments on Relevance: Australia Search Report PR 1005.
Supplementary European Search Report for EP 01 97 3835, dated Jan. 15, 2004.
Australian Patent Office International-Type Search Report, PR 0684, dated Dec. 20, 2000.
International Search Report for PCT/AU01/01231, dated Oct. 26, 2001.
Australian Patent Office International-Type Search Report, PR 0542 dated Dec. 20, 2000.
Australian Patent Office International-Type Search Report, PR 0807 dated Dec. 20, 2000.
International Search Report for PCT/AU01/01232, dated Oct. 26, 2001.
International Preliminary Examination Report, for PCT/AU01/01232 dated Feb. 25, 2002.
Australian Patent Office International-Type-Search Report, PR 0541 dated Dec. 20, 2000.
International Preliminary Examination Report for PCT/AU01/01230 dated Nov. 27, 2001.
International Search Report for PCT/AU01/01230 dated Oct. 26, 2001.

* cited by examiner

COCHLEAR IMPLANT ELECTRODE ARRAY

FIELD OF THE INVENTION

The present invention relates to an implantable device and, in particular, to an implantable cochlear electrode incorporating a bioresorbable stylet.

BACKGROUND OF THE INVENTION

Hearing loss, which may be due to many different causes, is generally of two types, conductive and sensorineural. Of these types, conductive hearing loss occurs where the normal mechanical pathways for sound to reach the hair cells in the cochlea are impeded, for example, by damage to the ossicles. Conductive hearing loss may often be helped by use of conventional hearing aid systems, which amplify sound so that acoustic information does reach the cochlea and the hair cells.

In many people who are profoundly deaf, however, the reason for deafness is sensorineural hearing loss. This type of hearing loss is due to the absence of, or destruction of, the hair cells in the cochlea which transduce acoustic signals into nerve impulses. These people are thus unable to derive suitable benefit from conventional hearing aid systems, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve. U.S. Pat. No. 4,532,930, the contents of which are incorporated herein by reference, provides a description of one type of traditional cochlear implant system.

Cochlear implant systems have typically consisted of two key components, namely an external component commonly referred to as a processor unit, and an implanted internal component commonly referred to as a stimulator/receiver unit. Traditionally, both of these components have cooperated together to provide the sound sensation to an implantee.

The external component has traditionally consisted of a microphone for detecting sounds, such as speech and environmental sounds, a speech processor that converts the detected sounds and particularly speech into a coded signal, a power source such as a battery, and an external antenna transmitter coil.

The coded signal output by the speech processor is transmitted transcutaneously to the implanted stimulator/receiver unit situated within a recess of the temporal bone of the implantee. This transcutaneous transmission occurs through use of an inductive coupling provided between the external antenna transmitter coil which is positioned to communicate with an implanted antenna receiver coil provided with the stimulator/receiver unit. This communication serves two essential purposes, firstly to transcutaneously transmit the coded sound signal and secondly to provide power to the implanted stimulator/receiver unit Conventionally, this link has been in the form of a radio frequency (RF) link, but other such links have been proposed and implemented with varying degrees of success.

The implanted stimulator/receiver unit typically included the antenna receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

The external componentry of the cochlear implant has been traditionally carried on the body of the implantee, such as in a pocket of the implantee's clothing, a belt pouch or in a harness, while the microphone has been mounted on a clip mounted behind the ear or on a clothing lapel of the implantee.

More recently, due in the main to improvements in technology, the physical dimensions of the speech processor have been able to be reduced allowing for the external componentry to be housed in a small unit capable of being worn behind the ear of the implantee. This unit has allowed the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit.

With continuing future technological advancements it will be possible to provide a cochlear implant system which is totally implanted within the head of the user and requires no external devices to operate. The microphone will be implanted within the user as well as a power source, so that there will be no need to require an external link for the device to operate, at least for a period of time.

Together with improvements in available technology much research has been undertaken in the area of understanding the way sound is naturally processed by the human auditory system. With such an increased understanding of how the cochlea naturally processes sounds of varying frequency and magnitude, there is a need to provide an improved cochlear implant system that delivers electrical stimulation to the auditory nerve in a way that takes into account the natural characteristics of the cochlea.

It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes, each electrode being arranged and constructed to deliver a cochlea-stimulating signal within a preselected frequency range to the appropriate cochlea region. The electrical currents and electric fields from each electrode stimulate the cilia disposed on the modiola of the cochlea. Several electrodes may be active simultaneously.

It has been found that in order for these electrodes to be effective, the magnitude of the currents flowing from these electrodes and the intensity of the corresponding electric fields, are a function of the distance between the electrodes and the modiola. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiola as small as possible. This is best accomplished by providing the electrode array in the shape which generally follows the shape of the modiola. Also, this way the delivery of the electrical stimulation to the auditory nerve is most effective as the electrode contacts are as close to the auditory nerves that are particularly responsive to selected pitches of sound waves.

In order to achieve this electrode array position close to the inside wall of the cochlea, the electrode needs to be designed in such a way that it assumes this position upon or immediately following insertion into the cochlea. This is a challenge, as the array needs to be shaped such that it assumes a curved shape to conform with the shape of the modiola and must also be shaped such that the insertion process causes minimal trauma to the sensitive structures of the cochlea. In this sense it has been found to be desirable for the electrode array be generally straight during the insertion procedure.

Several procedures have been adopted to provide an electrode assembly that is relatively straightforward to insert while adopting a curved configuration following insertion in the cochlea. In one case, a platinum wire stylet is used to hold a pre-curved electrode array in a generally straight configuration up until insertion. Following insertion, the platinum stylet is withdrawn allowing the array to return to its pre-curved configuration.

In another development, a bimetallic filament (such as nickel/titanium) or a shape memory alloy (such as an alloy of nickel and titanium) is positioned in the electrode assembly and used to again hold a pre-curved electrode array in a generally straight configuration while the array is at about room temperature. On insertion into the body and exposure to body temperature, the alloy or filament bends into a pre-selected curved configuration.

In a still further arrangement, a longitudinal element that is arranged on one side of the array and constructed to change its dimension on insertion can be utilised. For example, the longitudinal element could include a hydrogel, such as polyacrylic acid (PAA) or polyvinyl alcohol (PVA), which expands after insertion by absorbing water from the cochlear fluid.

In developing such electrode array designs, it is of great importance that the design be constructed to minimise potential damage to sensitive structures in the cochlear on insertion and placement. Each of the above constructions suffer from a number of disadvantages in this regard.

Still further, it has been proposed to straighten pre-curved electrode arrays using inserted longitudinal elements or surrounding sheaths formed from bioresorbable materials that dissolve or soften on implantation. A disadvantage with use of such bioresorbable materials is that, due to the generally wet nature of the surgical environment, the polymer can dissolve or soften before the electrode array is appropriately positioned, causing difficulties in placement and insertion procedures.

The present invention is directed to an electrode assembly adapted to overcome some of the difficulties of prior art electrode assemblies.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present invention relates to an implantable tissue stimulating device having a first configuration prior to and at least on commencement of insertion into an implantee's body and adapted to adopt at least a second configuration following insertion.

According to one aspect, the present invention is an implantable tissue-stimulating device comprising:

an elongate member having a plurality of electrodes mounted thereon and having a first configuration selected to allow said member to be inserted into an implantee's body and at least a second configuration wherein said elongate member is adapted to apply a preselected tissue stimulation with the electrodes, said elongate member being made of a resiliently flexible first material;

a bioresorbable stiffening element having a configuration selected for biassing said elongate member into said first configuration, said stiffening element being made of a second material relatively stiffer than said first material and which dissolves or softens on exposure to a fluid to permit said elongate member to at least approach or adopt said second configuration; and an outer layer surrounding the stiffening element, the layer being made of a material sufficiently resiliently flexible to allow said elongate member to at least approach or adopt said second configuration, the outer layer having a first rate of fluid ingress therethrough and having at least one fluid ingress means formed therein, the rate of fluid ingress through the fluid ingress means being greater than the first rate of fluid ingress through the outer layer.

In a preferred embodiment, the second configuration of the elongate member is curved. More preferably, the elongate member adopts a spiral configuration when in the second configuration.

In a further embodiment, the fluid is a saline solution. In another embodiment, the fluid is a body fluid of the implantee.

According to a second aspect, the present invention is a cochlear implant electrode assembly comprising:

an elongate electrode carrier member having a plurality of electrodes mounted thereon and having a first configuration selected to allow said member to be inserted into an implantee's cochlea and at least a second configuration wherein said elongate member is curved to match a surface of said cochlea, said elongate member being made of a resiliently flexible first material;

a bioresorbable stiffening element having a configuration selected for biassing said elongate member into said first configuration, said stiffening element being made of a second material relatively stiffer than said first material and which dissolves or softens on exposure to cochlear fluids to permit said elongate member to at least approach or adopt said second configuration; and an outer layer surrounding the stiffening element, the layer being made of a material sufficiently resiliently flexible to allow said elongate member to at least approach or adopt said second configuration, the outer layer having a first rate of cochlear fluid ingress therethrough and having at least one fluid ingress means formed therein, the rate of cochlear fluid ingress through the fluid ingress means being greater than the first rate of cochlear fluid ingress through the outer layer.

The elongate member is preferably preformed from a plastics material with memory and is preformed to the second configuration. The elongate member preferably has a first end that is firstly inserted into the implantee.

In a preferred embodiment, the first configuration is preferably substantially straight. More preferably, the first configuration is straight.

In a preferred embodiment, the elongate member is formed from a suitable biocompatible material. In one embodiment, the material can be a silicone, such as Silastic MDX 4-4210. In another embodiment, the elongate member can be formed from a polyurethane.

In a further embodiment, the elongate member can have a resiliently flexible tip member extending forwardly from the first end of the body. The tip member preferably has a distal end and a proximal end. The tip member can have a stiffness that is relatively less stiff than said stiffening element. The tip member can further be formed of a material that is substantially the same or the same stiffness as the body of the elongate member. In another embodiment, the tip member can be formed of a material that is relatively less stiff than at least a portion of the elongate member. In a further embodiment, the tip member can be formed of a material that undergoes a change in stiffness, preferably a decrease in stiffness, on insertion into the body, such as the cochlea.

In a further embodiment, the stiffness of the tip member can vary along at least a portion of its length from its distal end to its proximal end. In one embodiment, the stiffness of the tip member can vary over the entire length of the tip member or only a portion thereof. The stiffness can increase from the distal end to the proximal end. In one embodiment, the stiffness of the tip member over said portion or its length can increase gradually from its distal end towards to the proximal end. The increase in stiffness can be substantially smooth or increase in a stepwise fashion.

In a further embodiment, the tip member can be formed of the same material as the body of the elongate member. In another embodiment, the tip member can be formed of a different material to that of the body of the elongate member. The tip member can be comprised of an inner relatively stiff core of material having a tapered end, with at least the tapered end being overlaid by a relatively flexible material that extends beyond the tapered end of the core material so that the tip member undergoes a gradual decrease in flexibility in the region of the tapered end of the core moving away from the distal end.

The tip member can be formed separately to the body of the elongate member and mounted thereto. For example, the tip member can be adhered to the first end of the body of the elongate member. In another embodiment, the tip member can be integrally formed with the body of the elongate member. The tip member can be formed from a silicone material. In another embodiment, the tip member can be formed of an elastomeric material, such as polyurethane.

In another embodiment, the tip member can have a plurality of metallic particles dispersed therethrough. The metallic particles can be substantially evenly dispersed through the tip member. Alternatively, the metallic particles can be non-evenly dispersed throughout the tip member. In one embodiment, the metallic particles can increase in density away from the distal end towards the proximal end of the tip member. By varying the density of the metallic particles, it is possible to vary the relative stiffness of the tip member.

The metallic particles preferably comprise a biocompatible material, such as platinum. The particles can be substantially spherical or spherical. It will be appreciated that the particles can have other suitable shapes. In one embodiment, the particles can have a diameter between about 50 μm and 100 μm.

In addition to, or instead of, being used to potentially modify the physical characteristics of the tip member, the provision of the metallic particles also result in the tip member being detectable by fluoroscopy and X-ray techniques. This provides another means for the surgeon to monitor the placement and position of the tip member during or after insertion of the electrode array in the body, such as in the cochlea.

When the elongate member is in the first configuration, the tip member is preferably substantially straight and, more preferably, straight.

In a further embodiment, the tip member can be coated with a lubricious material. The lubricious material can be a bioresorbable or non-bioresorbable material.

The tip member can be formed from, or incorporate as a portion thereof, a bioresorbable material. The presence of the bioresorbable material preferably results in the flexibility of the tip member increasing on insertion of the tip member into the body, such as the cochlea. The bioresorbable material in the tip member can be selected from the group consisting of polyacrylic acid (PAA), polyvinyl alcohol (PVA), polylactic acid (PLA) and polyglycolic acid (PGA).

In another embodiment, the tip member can be formed from, or incorporate as a portion thereof, a polymeric coating which becomes softer, and so increases in resilient flexibility, in the presence of moisture or body heat.

The tip member preferably has a length from its distal end to its proximal end in the range of about 0.3 to 4 mm, more preferably about 1.0 to 3 mm. The diameter of the tip member can be substantially constant for a majority of its length or can vary in diameter. The tip member can be substantially cylindrical, cylindrical, or non-cylindrical for a majority of its length. At the distal end, the diameter preferably gradually decreases to form a rounded end. The maximum diameter of the tip member is preferably about 0.55 mm.

In one embodiment, the tip member can be solid. In another embodiment, the tip member can have an external wall defining a cavity. In one embodiment, the cavity can have a diameter greater than that of the receiving portion of the body of the elongate member. In a further embodiment, the cavity can extend from the proximal end towards the distal end of the tip member. The cavity can decrease in diameter away from the proximal end. The cavity can be in communication with a distal end of the receiving portion of the body of the elongate member. In a further embodiment, the stiffening means can extend into the cavity when positioned within the device or assembly according to the respective aspects of the present invention. In a preferred embodiment, the tip member can move relative to the stiffening means when it extends into the cavity of the tip member.

In general, the tip could be made of a combination of materials arranged in a variety of geometries depending on the specific design goal. The outside shape and size of the tip can also be made in a variety of forms depending on the design goal.

In a further embodiment, the bioresorbable material of the stiffening element is selected from the group consisting of polyacrylic acid (PAA), polyvinyl alcohol (PVA), polylactic acid (PLA) and polyglycolic acid (PGA). Other materials could also be used which provide the characteristics required for the particular application.

The outer layer can be in turn surrounded by another layer. In a further embodiment, the outer layer can be formed from a biocompatible material. In one embodiment, the outer layer can be formed from a material that has a relatively higher degree of resilient flexibility than the elongate member. In another embodiment, the material of the outer layer can have a resilient flexibility identical to that of the elongate member. In a preferred embodiment, the outer layer is formed from the same material as the elongate member.

The outer layer can be bonded to the elongate member. In another embodiment, the outer layer can be integrally formed therewith.

In one embodiment, the stiffening element can comprise a longitudinal quasi-stylet disposed in a lumen extending within the elongate member. In one embodiment, the lumen can be cylindrical or any other suitable shape and also can have an opening formed therein, providing the fluid ingress means of the assembly.

The opening is preferably at an end of the lumen distal the first end of the elongate member. In this embodiment, the opening can be closed by a closure means adapted to seal the opening of the lumen.

The closure means can comprise a plug adapted to be inserted into the lumen and to form a seal therewith. The plug can have a frusto-conical outer wall adapted to seal with the wall of the lumen on insertion. The plug in this embodiment can be formed from a resiliently flexible material such as silicone or polyurethane. Alternatively, the plug could be of any suitable shape and could also be formed from a stiff plastic such as polytetrafluoroethylene (PTFE) or a metal such as platinum or stainless steel.

In another embodiment, the closure means can comprise a cap adapted to seal the opening of the lumen. In one embodiment, the cap can have a top adapted to seal the opening and a skirt depending therefrom. The skirt can have an engagement means formed on an outer surface thereof adapted to engage with the inner surface of the lumen on mounting of the cap to the lumen. In this embodiment, the inner surface of the lumen can have an engagement means complementary to that on the outer surface of the skirt of the cap. The engagement means on the skirt can comprise a screw thread adapted to engage with a corresponding screw thread on the inner cylindrical surface of the lumen.

In another embodiment, the stiffening element can comprise a sheath that at least partially surrounds the elongate member. In this embodiment, the sheath preferably fully envelops the elongate member. In this embodiment, an annular channel can be formed in the elongate member to receive the sheath. Such an annular channel can have an annular opening at an end distal the first end of the elongate member. The annular opening of the channel can be closed by a suitably shaped plug or cap.

In another embodiment, the opening of the lumen or channel can be closed by a sealing layer bonded to the elongate member. The sealing layer can be formed from a layer of silicone material that is used to close the opening following placement of the stiffening element within the elongate member. In another embodiment, the elongate member can be fabricated such that the closure means is provided by an extension of the outer layer over the opening of the lumen or channel or a drop of silicone or other sealing material over the opening.

In the latter case, the closure means is preferably removable to form an opening by slicing the sealing layer or outer layer extension with a blade, such as that provided by a pair of scissors, to allow ingress of fluid into the lumen or channel.

In a further embodiment, a plurality of openings, comprising the fluid ingress means, can be formed in the outer layer. In one embodiment, the openings can be disposed along the length of the outer layer. In one embodiment, the openings can be equally spaced along the length of the outer layer. In a preferred embodiment, the openings can comprise slits formed in the outer layer. The slits preferably slow but do not prevent ingress of fluid through the outer layer to the stiffening element. In a further embodiment, the slits can be formed in a lateral surface of the elongate member such that on the commencement of curvature of the elongate member, the slits are caused to at least partially open and allow fluid ingress into the elongate member.

The slits can be formed to all allow substantially the same or the same rate of ingress of fluid through the outer layer. In another embodiment, at least one slit can allow a different rate of progress of fluid through the outer layer compared to the other slits. In a still further embodiment, each slit can allow a different rate of progress of fluid through the outer layer compared to the other slits formed therein.

In one embodiment, the slit most distal the first end of the elongate member can allow a greater rate of fluid ingress through the outer layer than its adjacent slit positioned closer to said first end or vice versa. As such, the bioresorbable material beneath this slit preferably begins to dissolve or soften before the remainder of the stiffening element so allowing the elongate member to begin to firstly move from its first configuration to its second configuration at or adjacent the position of this most distal or most proximal slit.

The rate of progress provided by each slit can follow this pattern along the length of the device towards the first end, with the next closer slit to the first end providing a relatively lesser rate of ingress than its adjacent more distal slit. This pattern results in the bioresorbable material dissolving or softening from an end distal the first end towards an end closer to the first end or vice versa. Where the first configuration is straight and the second configuration is curved, the elongate member begins to curve distal the first end and then continues to further adopt the curved configuration as the stiffening element dissolves or softens towards the first end or vice versa.

In one embodiment, the slits or other fluid ingress means can be sealable with a bioresorbable material. The bioresorbable material preferably softens and/or dissolves on exposure to a fluid, such as cochlear fluid, to allow ingress of the fluid into the elongate member. In this embodiment, the slits or other fluid ingress means can be sealed with the same or a different quantity and/or the same or different thicknesses of bioresorbable material. Variations in thickness and/or quantity of the bioresorbable material provide a means of varying the rate of ultimate dissolution of the stiffening element of the device.

In another embodiment, the fluid ingress means can comprise regions of silicone having a thickness less than that of the remainder of the outer layer. Due to the reduced thickness of these regions, the fluid passes through the fluid ingress means more quickly than the remainder of the outer layer. The thickness of the fluid ingress regions can be varied to suit the desired rate of dissolution/softening of the stiffening element required by the application. Different regions can have different thickness as required. For example, a region distal the first end of the elongate member can have a thickness that is thinner than that of a region closer to the first end.

In a further embodiment, at least a portion of an outer surface of the elongate member can have a coating of a lubricious material. In one embodiment, a substantial portion or the entire outer surface of the elongate member can have a coating of the lubricious material.

In this embodiment, the lubricious material can be selected from the group comprising polyacrylic acid (PAA), polyvinyl alcohol (PVA), polylactic acid (PLA) and polyglycolic acid (PGA). It is envisaged that other similar materials could also be used.

In a further aspect, the present invention comprises a method of implanting a tissue-stimulating device or cochlear electrode assembly device as defined herein in a body of an implantee.

In this aspect, the method can comprise a step of accessing the implantation site and then a step of inserting the device. Prior to insertion, the device is preferably substantially straight or straight. On insertion, the device can adopt an intermediate configuration (as defined herein). Either prior to full insertion or following full insertion, the device preferably adopts its second configuration.

Once implanted, the electrodes can receive stimulation signals from a stimulator means. The stimulator means is preferably electrically connected to the elongate member by way of an electrical lead. The lead can include the one or more wires extending from each electrode of the array mounted on the elongate member.

In one embodiment, the lead can extend from the elongate member to the stimulator means or at least the housing thereof. In one embodiment, the lead is continuous with no electrical connectors, at least external the housing of the stimulator means, required to connect the wires extending from the electrodes to the stimulator means. One advantage of this arrangement is that there is no requirement for the surgeon implanting the device to make the necessary electrical connection between the wires extending from the electrodes and the stimulator means.

The stimulator means is preferably positioned within a housing that is implantable within the implantee. The housing for the stimulator means is preferably implantable within the bony well in the bone behind the ear posterior to the mastoid.

When implantable, the housing preferably contains, in addition to the stimulator means, a receiver means. The receiver means is preferably adapted to receive signals from a controller means. The controller means is, in use, preferably mounted external to the body of the implantee such that the signals are transmitted transcutaneously through the implantee.

Signals can preferably travel from the controller means to the receiver means and vice versa. The receiver means can include a receiver coil adapted to receive radio frequency (RF) signals from a corresponding transmitter coil worn externally of the body. The radio frequency signals can comprise frequency modulated (FM) signals. While described as a receiver coil, the receiver coil can preferably transmit signals to the transmitter coil which receives the signals.

The transmitter coil is preferably held in position adjacent the implanted location of the receiver coil by way of respective attractive magnets mounted centrally in, or at some other position relative to, the coils.

The external controller can comprise a speech processor adapted to receive signals output by a microphone. During use, the microphone is preferably worn on the pinna of the implantee, however, other suitable locations can be envisaged, such as a lapel of the implantee's clothing. The speech processor encodes the sound detected by the microphone into a sequence of electrical stimuli following given algorithms, such as algorithms already developed for cochlear implant systems. The encoded sequence is transferred to the implanted stimulator/receiver means using the transmitter and receiver coils. The implanted stimulator/receiver means demodulates the FM signals and allocates the electrical pulses to the appropriate attached electrode by an algorithm which is consistent with the chosen speech coding strategy.

The external controller further comprises a power supply. The power supply can comprise one or more rechargeable batteries. The transmitter and receiver coils are used to provide power via transcutaneous induction to the implanted stimulator/receiver means and the electrode array.

While the implant system can rely on external componentry, in another embodiment, the controller means, including the microphone, speech processor and power supply can also be implantable. In this embodiment, the controller means can be contained within a hermetically sealed housing or the housing used for the stimulator means.

BRIEF DESCRIPTION OF THE DRAWINGS

By way of example only, preferred embodiments of the invention are now described with reference to the accompanying drawings, in which.

PREFERRED MODE OF CARRYING OUT THE INVENTION

Figure 1:
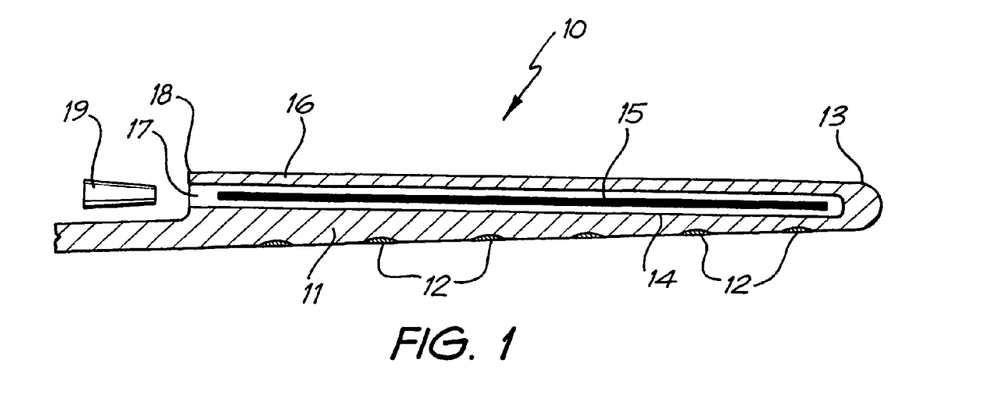
FIG. 1 is a simplified cross-sectional view of one embodiment of an electrode assembly according to the present invention.
Figure 3:
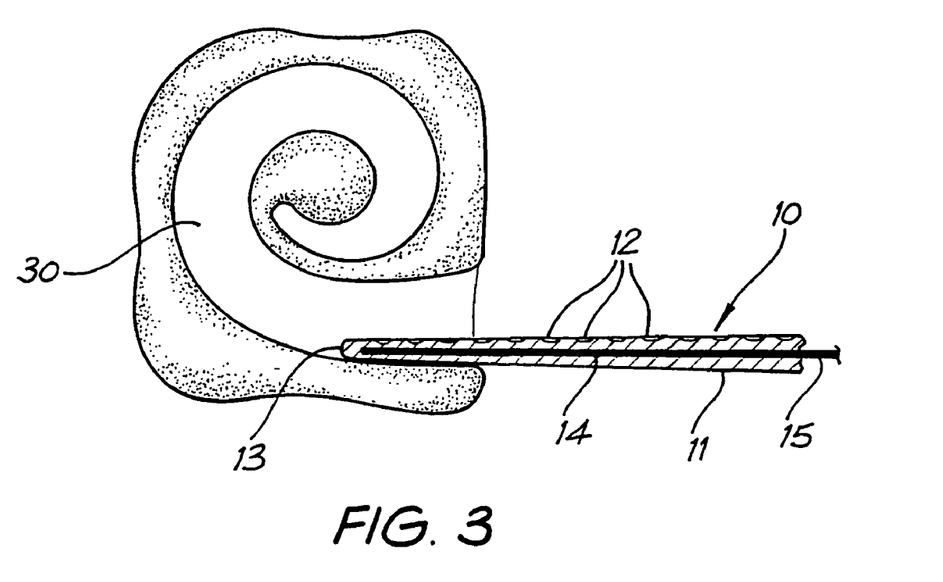
FIG. 3 is a diagrammatic view of the assembly of FIG. 1 being inserted in to the scala tympani.
Figure 4:
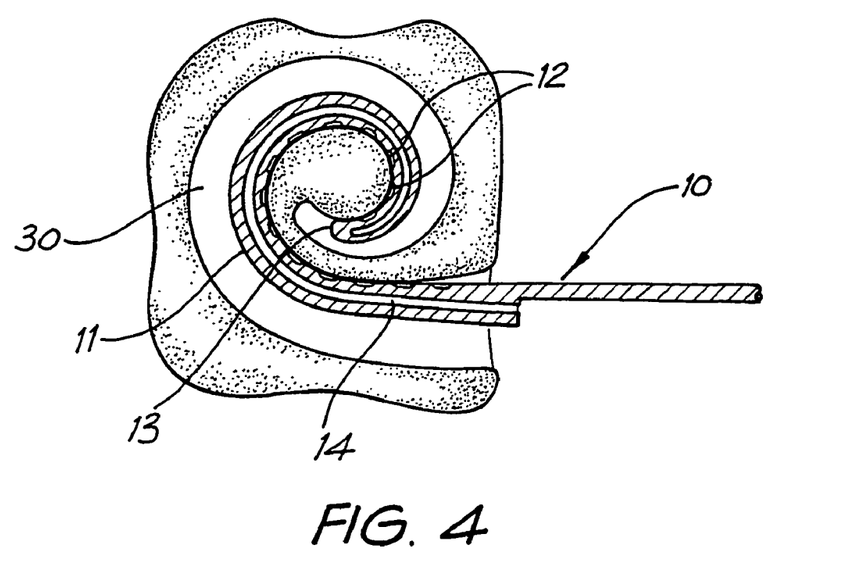
FIG. 4 is a diagrammatic view of the assembly of FIG. 1 deployed in the scala tympani.

One embodiment of a cochlear implant electrode assembly is depicted generally as 10 in FIGS. 1, 3 and 4.

The depicted electrode assembly 10 preferably has an electrical lead extending back to a stimulator/receiver housing. In considering this invention, it is to be understood that each electrode may have one or more wires (not depicted) electrically connected thereto and extending from each respective electrode back through the lead to the stimulator/receiver. The use of a stimulator/receiver as described herein is known in the art and the present invention can be used with any such stimulator/receiver as known in the art.

Figure 2:
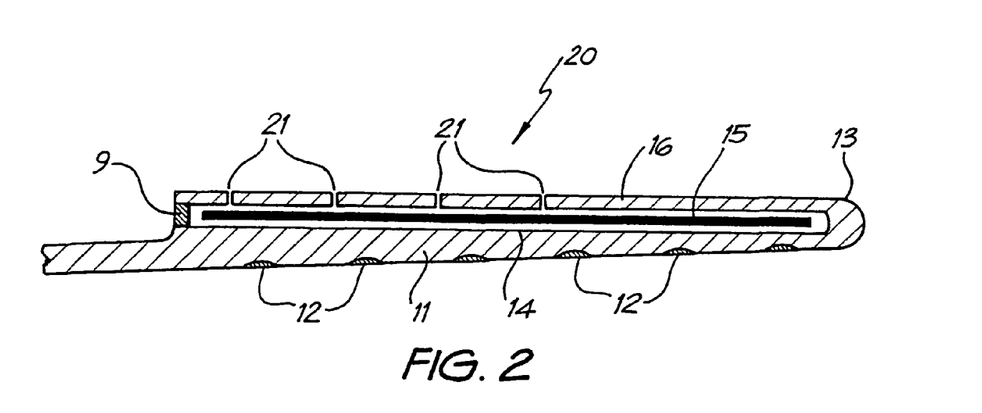
FIG. 2 is a simplified cross-sectional view of another embodiment of an electrode assembly according to the present invention.
Figure 5:
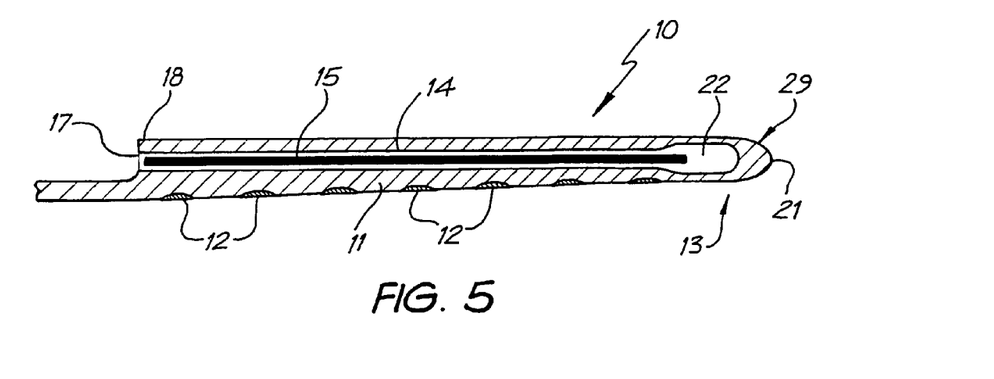
FIG. 5 is a simplified cross-sectional view of another embodiment of an electrode assembly according to the present invention.

The assembly 10 comprises an elongate electrode carrier member 11 having a plurality of electrodes 12 mounted thereon. For the purposes of clarity, the electrodes 12 depicted in FIGS. 1, 2 and 5 are not necessarily shown to scale. The depicted elongate member 11 is preformed from a resiliently flexible silicone with memory and is preformed to a curved configuration suitable for conforming with the inner wall of the scala tympani 30 of the cochlea as depicted in FIG. 4. The elongate member 11 has a first end 13, distal the lead, that is firstly inserted into the implantee on insertion of the assembly 10.

As depicted in FIG. 5, the elongate member 11 can have a tip member 29 integrally formed with its first end 13. The tip 29 is formed from the same silicone used to fabricate the elongate member 11 and, in the depicted embodiment, the material of tip member 29 has a resilient flexibility equal to that of the material used for the carrier member 11.

Figure 6A:
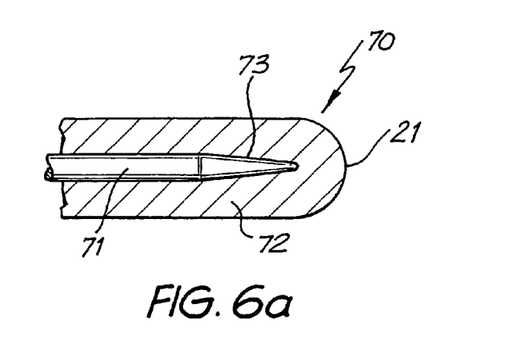
FIGS. 6a-6d depict alternative tip structures for the electrode assembly depicted in FIG. 5.

Possible alternative constructions for the tip member 29 are provided in FIGS. 6a-6d. As depicted in FIG. 6a, the tip member 70 can be solid and formed of an inner core 71 of relatively stiff material 71 and an outer layer 72 of relatively flexible material. The core 71 can taper in diameter over region 73 towards the distal end 21. The taper 73 causes the overall stiffness of the tip 70 to increase over the length of the taper 73 away from the distal end 21. The outer layer 72 can be formed of the same material as the remainder of the body of the elongate carrier member 11 or can be a different material.

Figure 6B:
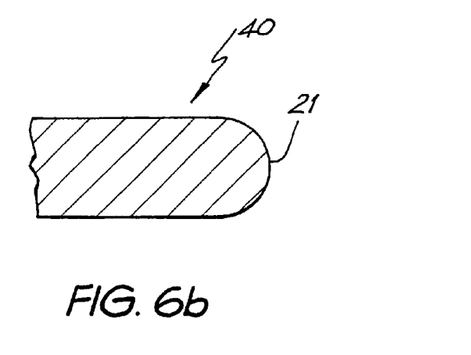

As depicted in FIG. 6b, the tip member 40 can comprise a solid mass integrally formed to the first end 13 of the elongate carrier 11.

Figure 6C:
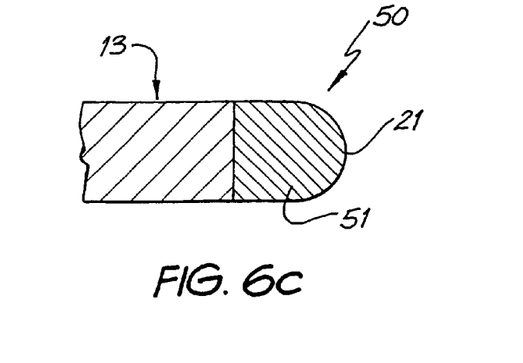

Still further and as depicted in FIG. 6c, the tip member 50 can comprise a solid mass 51 that is formed separately from the carrier member 11 and subsequently adhered thereto.

Figure 6D:
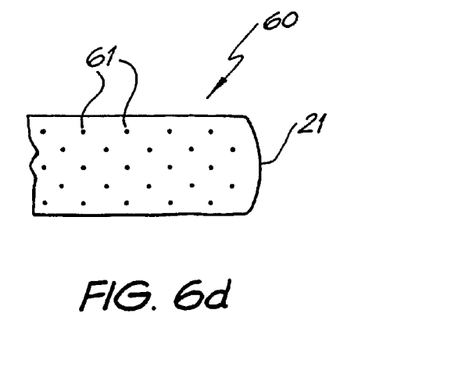

As depicted in FIG. 6d, the tip member 60 can comprise an elastomeric silicone material having a plurality of substantially spherical platinum particles 61 dispersed therethrough. The particles 61 have a diameter between about 50 µm and 100 µm. It will be appreciated that the particles 61 depicted in FIG. 6d are not drawn to scale.

In FIG. 6d, the particles 61 are depicted as substantially evenly dispersed through the tip member 60. In another embodiment, the particles could be non-evenly dispersed through the tip member. For example, the particles could increase in density away from the distal end 21 towards the proximal end of the tip member 60. By varying the density of the platinum particles 61, it is possible to vary the relative stiffness of the tip member 60.

In addition to, or instead of, being used to potentially modify the physical characteristics of the tip member, the provision of the metallic particles 61 also result in the tip member 60 being detectable by fluoroscopy and X-ray techniques. This provides another means for the surgeon to either monitor the placement and position of the tip member 60 during or after insertion of the electrode array 10 in an implantee's cochlea.

Disposed within a substantially cylindrical lumen 14 is a stylet-type element 15. This stylet-type element 15 differs from a conventional stylet in that it is formed from a bioresorbable polyacrylic acid (PAA) that is adapted to dissolve or soften on exposure to fluids to permit the elongate member 11 to take its preformed curved configuration. It will be appreciated that the stylet could be formed from other suitable bioresorbable materials. The stylet-type element 15 has a straight configuration and has a stiffness greater than that of the silicone making up the elongate member 11. Accordingly, the stylet-type element 15, when in position biases the elongate member 11 into a straight configuration as depicted in FIGS. 1 and 3.

Overlaying the stylet-type element 15 is an integral outer layer 16 of silicone material that surrounds and protects the stylet-type element 15. In particular, the outer layer 16 serves to protect the stylet-type element 15, at least for some time, from dissolution or softening due to exposure of the assembly to fluids, such as cochlear fluids, on insertion in the scala tympani 30.

As depicted in FIG. 1, the lumen 14 has an opening 17 at an end 18 distal the first end 13. In the embodiment depicted in FIG. 1, the opening 17 can be closed by a plug 19 that is adapted to seal the opening 17 of the lumen 14. While a frusto-conical plug is depicted in FIG. 1, other plug types can be envisaged. For example, and as is depicted in FIG. 2, the opening 17 can be sealed with a quantity 9 of silicone.

As an alternative to the plug 19 depicted in FIG. 1, the opening 17 of the lumen 14 can be closed by a sealing layer bonded to the elongate member 11. The sealing layer can be formed from a layer of silicone material that is used to close the opening 17 following placement of the stylet-type element 15 within the lumen 14. In another alternative, the elongate member can be fabricated such that the closure is provided by an extension of the outer layer 16 over the opening 17 of the lumen 14.

In the latter case, the closure is preferably removed to form the opening 17 by slicing the sealing layer or outer layer extension with a blade, such as that provided by a pair of scissors, to allow ingress of fluid into the lumen 14.

An alternative embodiment of the electrode array is depicted generally as 20 in FIG. 2. In this embodiment, a plurality of transverse slits 21 are formed in the outer layer 16. The slits preferably slow but do not prevent ingress of fluid through the outer layer 16 to the stylet-type element 15.

In the depicted embodiment, each slit 21 is adapted to allow a substantially equal rate of ingress of fluid into the lumen 14. It will be appreciated that the slit design could be modified such that different slits 21 allowed different rates of progress of fluid through the outer layer 16. For example, a slit 21 most distal the first end 13 could be adapted to allow a greater rate of fluid ingress through the outer layer 16 than its adjacent slit positioned closer to the first end 13. In this case, the bioresorbable material of the stylet-type element 15 beneath this slit would begin to dissolve or soften before the remainder of the stylet-type element 15 so allowing the elongate member 11 to begin to move from the straight configuration to its curved configuration at or adjacent the position of this most distal slit 21. In the depicted embodiment, each slit 21 can also be filled with a quantity of bioresorbable material. In this case, each slit 21 can be filled with a different quantity or thickness of bioresorbable material so as to provide a means of controlling the location of and rate of dissolution of the stylet-type element 15.

The rate of progress provided by each slit 21 can follow this pattern along the length of the elongate member 11 towards the first end 13, with the next closer slit 21 to the first end 13 providing a relatively lesser rate of ingress than its adjacent more distal slit 21. This pattern results in the bioresorbable material of the stylet-type element 15 dissolving or softening from an end distal the first end 13 towards an end closer to the first end 13. As such, the straight elongate member 11 begins to curve distal the first end 13 and then continues to further adopt the curved configuration as the stylet-type element 15 dissolves or softens towards the first end 13 or vice versa.

As an alternative to the slits 21, the outer layer 16 of the elongate member 11 can be provided with one or more regions that more readily allow ingress of bodily fluids, such as cochlear fluids. These regions can comprise regions of the outer layer 16 that have a thickness less than that of the remainder of the outer layer 16. Due to the reduced thickness of these regions, the fluid passes through the regions more quickly than the remainder of the outer layer 16. The thickness of the fluid ingress regions can be varied to suit the desired rate of dissolution of the stylet-type element 15 required by the application. Different regions can have different thickness as required. For example, a region distal the first end 13 of the elongate member 11 can have a thickness that is thinner than that of a region closer to the first end 13, or vice versa. Such regions may also be formed by a matrix of pinholes or other such structure to allow for a chosen rate of fluid ingress rather than slits.

In use, the substantially straight assembly 10 or 20 will initially be positioned at an entry to the scala tympani 30 as depicted in FIG. 3. At this point, in those embodiments where present, the plug 19, or quantity 9, can be removed or a covering over the slits 21 peeled away to allow bodily fluids, such as cochlear fluids, to move into the lumen 14. Entry of the fluids into the lumen 14 commences dissolution or softening of the stylet-type element 15.

As dissolution or softening is occurring, the assembly 10 can be carefully advanced into the scala tympani 30. Dissolution or softening of the stylet-type element 15 causes the assembly 10 to begin to adopt a curved configuration. As the assembly 10 continues to be advanced, it is preferably positioned as depicted in FIG. 4, with the electrodes 12 facing the modiola within the cochlea so that they are positioned as close as possible to the spiral ganglia thereof.

The control of the commencement of, and preferably the rate of, stylet dissolution provides the surgeon with greater control of the implantation procedure for the cochlear implant electrode assembly 10. The provision of greater control minimises the potential for trauma to the sensitive tissues inside the cochlea and also enhances the likelihood of successful placement of the assembly 10 at the first attempt.

While the preferred embodiment of the invention has been described in conjunction with a cochlear implant, it is to be understood that the present invention has wider application to other implantable electrodes, such as electrodes used with pacemakers.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An implantable tissue-stimulating device comprising:
    an elongate carrier member having at least one electrode mounted thereon and having a first insertion configuration selected to allow said elongate carrier member to be inserted into an implantee's body and at least a second implanted configuration, wherein said elongate carrier member is made of a resiliently flexible first material;
    a bioresorbable stiffening element disposed in a lumen of the elongate carrier member and the bioresorbable stiffening element having a configuration selected for biasing said elongate carrier member into said first insertion configuration, said bioresorbable stiffening element being made of a second material relatively stiffer than said first material wherein said second material dissolves on exposure to a fluid to permit said elongate carrier member to substantially adopt said second implanted configuration while in the implantee's body; and
    an outer layer surrounding the bioresorbable stiffening element and the elongate carrier member, the outer layer being made of a material sufficiently resiliently flexible to allow said elongate carrier member to substantially adopt said second implanted configuration, and wherein the outer layer has at least one fluid ingress means formed therein.

2. An implantable tissue-stimulating device of claim 1 wherein the second configuration of the elongate carrier member is curved.

3. An implantable tissue-stimulating device of claim 2 wherein the elongate carrier member adopts a spiral configuration when in the second configuration.

4. An implantable tissue-stimulating device of claim 1 wherein the fluid is a body fluid of the implantee.

5. An implantable tissue-stimulating device of claim 1 wherein the elongate carrier member is preformed from a plastics material with memory and is preformed in the second configuration.

6. An implantable tissue-stimulating device of claim 1 wherein the elongate carrier member has a first end that is firstly inserted into the implantee.

7. An implantable tissue-stimulating device of claim 1 wherein the first configuration is at least substantially straight.

8. An implantable tissue-stimulating device of claim 1 wherein the elongate carrier member is formed from a biocompatible material.

9. An implantable tissue-stimulating device of claim 1 wherein the bioresorbable material of the bioresorbable stiffening element is selected from the group comprising polyacrylic acid (PAA), polyvinyl alcohol (PVA), polylactic acid (PLA) and polyglycolic acid (PCA).

10. An implantable tissue-stimulating device of claim 1 wherein the outer layer is in turn surrounded by an additional layer formed from a material selected from the group comprising a lubricious material and a non-lubricious material.

11. An implantable tissue-stimulating device of claim 10 wherein the outer layer is formed from a biocompatible material.

12. An implantable tissue-stimulating device of claim 1 wherein the lumen has at least one opening at an end of the lumen distal the first end of the elongate carrier member, the opening being closable by a closure means.

13. An implantable tissue-stimulating device of claim 12 wherein the closure means comprises a plug or cap.

14. An implantable tissue-stimulating device of claim 12 wherein the closure means comprises a sealing layer bonded to the elongate carrier member.

15. An implantable tissue-stimulating device of claim 1 wherein a plurality of the fluid ingress means in the form of slits are provided in the outer layer.

16. An implantable tissue-stimulating device of claim 15 wherein the slits are sealable with a bioresorbable material.

17. An implantable tissue-stimulating device of claim 15 wherein the slits are formed so as to have substantially the same rate of ingress of the fluid through the outer layer.

18. An implantable tissue-stimulating device of claim 15 wherein at least one slit has a different rate of progress of the fluid through the outer layer compared to the other slits in the outer layer.

19. An implantable tissue-stimulating device of claim 18 wherein a distal slit most distal to a first end of the elongate carrier member allows a greater rate of fluid ingress through the outer layer than its adjacent proximal slit positioned closer to the first end, such that the bioresorbable material of the bioresorbable stiffening element beneath said distal slit preferably begins to dissolve before the remainder of the bioresorbable stiffening element so allowing the elongate carrier member to begin to firstly move from its first configuration to its second configuration at or adjacent the position of the distal slit.

20. An implantable tissue-stimulating device of claim 18 wherein the rate of ingress provided by each slit follows a pattern of a relatively lesser rate in the rate of ingress from a distal slit most distal to a first end of the elongate carrier member towards a proximal slit most proximal to the first end of the elongate carrier member.

21. An implantable tissue-stimulating device of claim 1 wherein a plurality of fluid ingress means are provided in the outer layer and each fluid ingress means comprise regions of silicone having a thickness less than that of the outer layer.

22. An implantable tissue-stimulating device of claim 1 wherein a resiliently flexible tip member extends forwardly from a first end of the elongate carrier member.

23. An implantable tissue-stimulating device of claim 22 wherein the resiliently flexible tip member has a plurality of metallic particles dispersed therethrough.

24. A cochlear implant electrode assembly comprising:
an elongate carrier member having at least one electrode mounted thereon and having a first insertion configuration selected to allow said elongate carrier member to be inserted into an implantee's cochlea and at least a second implanted configuration to allow said elongate carrier member to substantially approximate a curve of said cochlea, wherein said elongate carrier member is made of a resiliently flexible first material;
a bioresorbable stiffening element disposed in a lumen of the elongate carrier member and the bioresorbable stiffening element having a configuration selected for biasing said elongate carrier member into said first insertion configuration, said bioresorbable stiffening element being made of a second material relatively stiffer than said first material, wherein said bioresorbable stiffening element dissolves on exposure to cochlear fluids to permit said elongate carrier member to substantially adopt said second implanted configuration; and
an outer layer surrounding the bioresorbable stiffening element and the elongate carrier member, the outer layer is made of a material sufficiently resiliently flexible to allow said elongate carrier member to substantially adopt said second implanted configuration, and wherein the outer layer includes at least one fluid ingress means formed therein.

25. A cochlear implant electrode assembly of claim 24 wherein the elongate carrier member is preformed from a plastics material with memory and is preformed in the second configuration.

26. A cochlear implant electrode assembly of claim 24 wherein the elongate carrier member has a first end that is firstly inserted into the implantee.

27. A cochlear implant electrode assembly of claim 24 wherein the first configuration is at least substantially straight.

28. A cochlear implant electrode assembly of claim 24 wherein the elongate carrier member is formed from a biocompatible material.

29. A cochlear implant electrode assembly of claim 24 wherein the bioresorbable material of the bioresorbable stiffening element is selected from the group comprising polyacrylic acid (PAA), polyvinyl alcohol (PVA), polylactic acid (PLA) and polyglycolic acid (PCA).

30. A cochlear implant electrode assembly of claim 24 wherein the outer layer is in turn surrounded by an additional layer formed from a material selected from the group comprising a lubricious material and a non-lubricious material.

31. A cochlear implant electrode assembly of claim 30 wherein the outer layer is formed from a biocompatible material.

32. A cochlear implant electrode assembly of claim 24 wherein the lumen has at least one opening at an end of the lumen distal the first end of the elongate carrier member, the opening being closable by a closure means.

33. A cochlear implant electrode assembly of claim 32 wherein the closure means comprises a plug or cap.

34. A cochlear implant electrode assembly of claim 32 wherein the closure means comprises a sealing layer bonded to the elongate carrier member.

35. A cochlear implant electrode assembly of claim 24 wherein a plurality of the fluid ingress means in the form of slits are provided in the outer layer.

36. A cochlear implant electrode assembly of claim 35 wherein the slits are formed so as to have substantially the same rate of ingress of the cochlear fluids through the outer layer.

37. A cochlear implant electrode assembly of claim 35 wherein at least one slit has a different rate of progress of the cochlear fluids through the outer layer compared to the other slits in the outer layer.

38. A cochlear implant electrode assembly of claim 37 wherein a distal slit most distal to a first end of the elongate carrier member allows a greater rate of fluid ingress through the outer layer than its adjacent proximal slit positioned closer to said first end, such that the bioresorbable material of the bioresorbable stiffening element beneath said distal slit preferably begins to dissolve before the remainder of the bioresorbable stiffening element so allowing the elongate carrier member to begin to firstly move from its first configuration to its second configuration at or adjacent the position of the distal slit.

39. A cochlear implant electrode assembly of claim 37 wherein the rate of ingress provided by each slit follows a pattern of a relatively lesser rate in the rate of ingress from a distal slit most distal to a first end of the elongate carrier member towards a proximal slit most proximal to the first end of the elongate carrier member.

40. A cochlear implant electrode assembly of claim 35 wherein the slits are sealable with a bioresorbable material.

41. A cochlear implant electrode assembly of claim 24 wherein a plurality of fluid ingress means are provided in the outer layer and each fluid ingress means comprise regions of silicone having a thickness less than that of the outer layer.

42. A cochlear implant electrode assembly of claim 24 wherein a resiliently flexible tip member extends forwardly from a first end of the elongate carrier member.

43. A cochlear implant electrode assembly of claim 42 wherein the resiliently flexible tip member has a plurality of metallic particles dispersed therethrough.

44. A cochlear implant electrode assembly of claim 24 wherein the second configuration of the elongate carrier member is curved.

45. A cochlear implant electrode assembly of claim 44 wherein the elongate carrier member adopts a spiral configuration when in the second configuration.

46. A cochlear implant electrode assembly comprising:
an elongate carrier member having at least one electrode mounted thereon and having a first insertion configuration selected to allow said elongate carrier member to be inserted into an implantee's cochlea and at least a second implanted configuration to allow said elongate carrier member to substantially approximate a curve of said cochlea, wherein said elongate carrier member is made of a resiliently flexible first material;
a bioresorbable stiffening element disposed in a lumen of the carrier member and having a configuration selected for biasing said elongate carrier member into said first insertion configuration, said bioresorbable stiffening element being made of a second material relatively stiffer than said first material, wherein said bioresorbable stiffening element dissolves on exposure to cochlear fluids to permit said elongate carrier member to substantially adopt said second implanted configuration; and an outer layer surrounding the bioresorbable stiffening element and the elongate carrier member, the outer layer is made of a material sufficiently resiliently flexible to allow said elongate carrier member to substantially adopt said second implanted configuration, and wherein the outer layer includes plurality of fluid ingress means and each fluid ingress means comprise regions of silicone having a thickness less than that of the outer layer.

47. An implantable tissue-stimulating device of claim 46 wherein the second implanted configuration of the elongate carrier member is curved.

48. An implantable tissue-stimulating device of claim 47 wherein the elongate carrier member adopts a spiral configuration when in the second implanted configuration.

49. A cochlear implant electrode assembly of claim 46 wherein the elongate carrier member is preformed from a plastics material with memory and is preformed in the second implanted configuration.

50. A cochlear implant electrode assembly of claim 46 wherein the elongate carrier member has a first end that is firstly inserted into the implantee.

51. A cochlear implant electrode assembly of claim 46 wherein the first configuration is at least substantially straight.

52. A cochlear implant electrode assembly of claim 46 wherein the elongate carrier member is formed from a biocompatible material.

53. A cochlear implant electrode assembly of claim 46 wherein the bioresorbable material of the bioresorbable stiffening element is selected from the group comprising polyacrylic acid (PAA), polyvinyl alcohol (PVA), polylactic acid (PLA) and polyglycolic acid (PCA).

54. A cochlear implant electrode assembly of claim 46 wherein the outer layer is in turn surrounded by an additional layer formed from a material selected from the group comprising a lubricious material and a non-lubricious material.

55. A cochlear implant electrode assembly of claim 54 wherein the outer layer is formed from a biocompatible material.

56. A cochlear implant electrode assembly of claim 46 wherein the bioresorbable stiffening element is positionable in a lumen extending within the elongate carrier member.

57. A cochlear implant electrode assembly of claim 56 wherein the lumen has at least one opening at an end of the lumen distal the first end of the elongate carrier member, the opening being closable by a closure means.

58. A cochlear implant electrode assembly of claim 57 wherein the closure means comprises a plug or cap.

59. A cochlear implant electrode assembly of claim 58 wherein the closure means comprises a sealing layer bonded to the elongate carrier member.

60. A cochlear implant electrode assembly of claim 46 wherein a plurality of the plurality of fluid ingress means in the form of slits are provided in the outer layer.

61. A cochlear implant electrode assembly of claim 60 wherein the slits are formed so as to have substantially the same rate of ingress of the cochlear fluids through the outer layer.

62. A cochlear implant electrode assembly of claim 60 wherein at least one slit has a different rate of progress of the cochlear fluids through the outer layer compared to the other slits in the outer layer.

63. A cochlear implant electrode assembly of claim 62 wherein a distal slit most distal to a first end of the elongate carrier member allows a greater rate of fluid ingress through the outer layer than its adjacent proximal slit positioned closer to said first end, such that the bioresorbable material of the bioresorbable stiffening element beneath said distal slit preferably begins to dissolve before the remainder of the bioresorbable stiffening element so allowing the elongate carrier member to begin to firstly move from its first configuration to its second configuration at or adjacent the position of the distal slit.

64. A cochlear implant electrode assembly of claim 62 wherein the rate of ingress provided by each slit follows a pattern of a relatively lesser rate in the rate of ingress from a distal slit most distal to a first end of the elongate carrier member towards a proximal slit most proximal to the first end of the elongate carrier member.

65. A cochlear implant electrode assembly of claim 60 wherein the slits are sealable with a bioresorbable material.

66. A cochlear implant electrode assembly of claim 46 wherein a resiliently flexible tip member extends forwardly from a first end of the elongate carrier member.

67. A cochlear implant electrode assembly of claim 66 wherein the resiliently flexible tip member has a plurality of metallic particles dispersed therethrough.

68. A cochlear implant electrode assembly of claim 46 wherein the second implanted configuration of the elongate carrier member is curved.

69. A cochlear implant electrode assembly of claim 68 wherein the elongate carrier member adopts a spiral configuration when in the second implanted configuration.

70. A cochlear implant electrode assembly comprising:

an elongate carrier member having at least one electrode mounted thereon and having a first insertion configuration selected to allow said elongate carrier member to be inserted into an implantee's cochlea and at least a second implanted configuration to allow said elongate carrier member to substantially approximate a curve of said cochlea, wherein said elongate carrier member is made of a resiliently flexible first material;

a bioresorbable stiffening element stiffening element disposed in a lumen of the carrier member and having a configuration selected for biasing said elongate carrier member into said first insertion configuration, said bioresorbable stiffening element being made of a second material relatively stiffer than said first material, wherein said bioresorbable stiffening element dissolves on exposure to cochlear fluids to permit said elongate carrier member to substantially adopt said second implanted configuration; and an outer layer surrounding the bioresorbable stiffening element and the elongate carrier member, the outer layer is made of a material sufficiently resiliently flexible to allow said elongate carrier member to substantially adopt said second implanted configuration, and wherein the outer layer includes a plurality of slits formed therein so as to have substantially the same rate of ingress of the cochlear fluids through the outer layer.

71. An implantable tissue-stimulating device of claim 70 wherein the second implanted configuration of the elongate carrier member is curved.

72. An implantable tissue-stimulating device of claim 71 wherein the elongate carrier member adopts a spiral configuration when in the second implanted configuration.

73. A cochlear implant electrode assembly of claim 70 wherein the elongate carrier member is preformed from a plastics material with memory and is preformed in the second implanted configuration.

74. A cochlear implant electrode assembly of claim 70 wherein the first configuration is at least substantially straight.

75. A cochlear implant electrode assembly of claim 70 wherein the elongate carrier member is formed from a biocompatible material.

76. A cochlear implant electrode assembly of claim 70 wherein the bioresorbable material of the bioresorbable stiffening element is selected from the group comprising polyacrylic acid (PAA), polyvinyl alcohol (PVA), polylactic acid (PLA) and polyglycolic acid (PCA).

77. A cochlear implant electrode assembly of claim 70 wherein the outer layer is in turn surrounded by an additional layer formed from a material selected from the group comprising a lubricious material and a non-lubricious material.

78. A cochlear implant electrode assembly of claim 77 wherein the outer layer is formed from a biocompatible material.

79. A cochlear implant electrode assembly of claim 70 wherein the lumen has at least one opening at an end of the lumen distal the first end of the elongate carrier member, the opening being closable by a closure means.

80. A cochlear implant electrode assembly of claim 79 wherein the closure means comprises a plug or cap.

81. A cochlear implant electrode assembly of claim 79 wherein the closure means comprises a sealing layer bonded to the elongate carrier member.

82. A cochlear implant electrode assembly of claim 70 wherein each of the plurality of slits are sealable with a bioresorbable material.

83. A cochlear implant electrode assembly of claim 70 wherein a resiliently flexible tip member extends forwardly from a first end of the elongate carrier member.

84. A cochlear implant electrode assembly of claim 83 wherein the resiliently flexible tip member has a plurality of metallic particles dispersed therethrough.

85. A cochlear implant electrode assembly of claim 70 wherein the second implanted configuration of the elongate carrier member is curved.

86. A cochlear implant electrode assembly of claim 85 wherein the elongate carrier member adopts a spiral configuration when in the second implanted configuration.

87. A cochlear implant electrode assembly comprising:

an elongate carrier member having at least one electrode mounted thereon and having a first insertion configuration selected to allow said elongate carrier member to be inserted into an implantee's cochlea and at least a second implanted configuration to allow said elongate carrier member to substantially approximate a curve of said cochlea, wherein said elongate carrier member is made of a resiliently flexible first material;

a bioresorbable stiffening element having a configuration selected for biasing said elongate carrier member into said first insertion configuration, said bioresorbable stiffening element being made of a second material relatively stiffer than said first material, wherein said bioresorbable stiffening element dissolves on exposure to cochlear fluids to permit said elongate carrier member to substantially adopt said second implanted configuration; and an outer layer surrounding the bioresorbable stiffening element and the elongate carrier member, the outer layer is made of a material sufficiently resiliently flexible to allow said elongate carrier member to substantially adopt said second implanted configuration, and wherein the outer layer includes a plurality of slits formed therein so at least one slit of the plurality of slits has a different rate of progress of the cochlear fluids through the outer layer compared to the other slits in the outer layer.

88. A cochlear implant electrode assembly of claim 87 wherein a distal slit most distal to a first end of the elongate carrier member allows a greater rate of fluid ingress through the outer layer than its adjacent proximal slit positioned closer to said first end, such that the bioresorbable material of the bioresorbable stiffening element beneath said distal slit preferably begins to dissolve before the remainder of the bioresorbable stiffening element so allowing the elongate carrier member to begin to firstly move from its first configuration to its second configuration at or adjacent the position of the distal slit.

89. A cochlear implant electrode assembly of claim 87 wherein the rate of ingress provided by each slit follows a pattern of a relatively lesser rate in the rate of ingress from a distal slit most distal to a first end of the elongate carrier member towards a proximal slit most proximal to the first end of the elongate carrier member.

90. An implantable tissue-stimulating device of claim 87 wherein the second implanted configuration of the elongate carrier member is curved.

91. An implantable tissue-stimulating device of claim 90 wherein the elongate carrier member adopts a spiral configuration when in the second implanted configuration.

92. A cochlear implant electrode assembly of claim 87 wherein the elongate carrier member is preformed from a plastics material with memory and is preformed in the second implanted configuration.

93. A cochlear implant electrode assembly of claim 87 wherein the elongate carrier member has a first end that is firstly inserted into the implantee.

94. A cochlear implant electrode assembly of claim 87 wherein the first configuration is at least substantially straight.

95. A cochlear implant electrode assembly of claim 87 wherein the elongate carrier member is formed from a biocompatible material.

96. A cochlear implant electrode assembly of claim 87 wherein the bioresorbable material of the bioresorbable stiffening element is selected from the group comprising polyacrylic acid (PAA), polyvinyl alcohol (PVA), polylactic acid (PLA) and polyglycolic acid (PCA).

97. A cochlear implant electrode assembly of claim 87 wherein the outer layer is in turn surrounded by an additional layer formed from a material selected from the group comprising a lubricious material and a non-lubricious material.

98. A cochlear implant electrode assembly of claim 97 wherein the outer layer is formed from a biocompatible material.

99. A cochlear implant electrode assembly of claim 87 wherein the bioresorbable stiffening element is positionable in a lumen extending within the elongate carrier member.

100. A cochlear implant electrode assembly of claim 99 wherein the lumen has at least one opening at an end of the lumen distal the first end of the elongate carrier member, the opening being closable by a closure means.

101. A cochlear implant electrode assembly of claim 100 wherein the closure means comprises a plug or cap.

102. A cochlear implant electrode assembly of claim 101 wherein the closure means comprises a sealing layer bonded to the elongate carrier member.

103. A cochlear implant electrode assembly of claim 87 wherein each of the plurality of slits are sealable with a bioresorbable material.

104. A cochlear implant electrode assembly of claim 87 wherein a resiliently flexible tip member extends forwardly from a first end of the elongate carrier member.

105. A cochlear implant electrode assembly of claim 104 wherein the resiliently flexible tip member has a plurality of metallic particles dispersed therethrough.

106. A cochlear implant electrode assembly of claim 87 wherein the second implanted configuration of the elongate carrier member is curved.

107. A cochlear implant electrode assembly of claim 106 wherein the elongate carrier member adopts a spiral configuration when in the second implanted configuration.

* * * * *